United States Patent [19]

Lewis

[11] 4,364,380
[45] Dec. 21, 1982

[54] DEVICE FOR USE IN INTERDENTAL ARCH WIRING

[76] Inventor: Michael Lewis, 10067-98 St., Grande Prairie, Alberta, Canada, T8V 2E7

[21] Appl. No.: 288,715

[22] Filed: Jul. 31, 1981

[51] Int. Cl.³ ............................................. A61F 5/04
[52] U.S. Cl. ..................... 128/89 A; 433/2; 433/18; 132/91; 174/94 R; 254/134.3 FT; 156/158
[58] Field of Search .......... 433/15, 2, 20, 18, 19, 433/22, 24, 148, 3; 132/93, 91, 89; 128/89 A, 326, 335.5; 174/94 R; 254/134.3 FT, 134.3 R; 428/379, 364; 156/158; 223/102, 103

[56] References Cited

U.S. PATENT DOCUMENTS

| 342,725 | 5/1886 | Arnold | 223/102 |
| 1,214,197 | 1/1917 | McAllister | 433/148 |
| 1,863,717 | 6/1932 | Holden | 223/102 |
| 1,986,974 | 1/1935 | Kellogg | 156/158 |
| 2,086,656 | 7/1937 | Woodward | 128/89 A |
| 2,522,794 | 9/1950 | Medof | 132/93 |
| 2,591,063 | 1/1952 | Goldberg | 128/335.5 |
| 3,394,704 | 7/1968 | Dery | 223/102 |

OTHER PUBLICATIONS

"A Useful Hint for Fracture Wiring", Dental Digest, 6-1934, C. L. Meistroff, p. 216.

Primary Examiner—Gene Mancene
Assistant Examiner—John J. Wilson
Attorney, Agent, or Firm—Rogers, Bereskin & Parr

[57] ABSTRACT

A device is disclosed for fitting a fracture wire around a tooth as part of an interdental arch wiring technique. In a preferred embodiment of the invention, the wire is U-shaped and the ends of a loop of dental floss are secured to respectively opposite end portions of the wire. Portions of the dental floss loop adjacent the ends of the wire are inserted downwardly into the respective interdental spaces on opposite sides of the tooth in question and the dental floss is then used to lead the wire into those spaces and to a position in which the bight of the wire embraces the tooth.

7 Claims, 6 Drawing Figures

DEVICE FOR USE IN INTERDENTAL ARCH WIRING

This invention is concerned generally with the surgical technique known as "interdental arch wiring", which is used in setting broken jawbones; more particularly, the invention is concerned with a device for use in performing this technique.

Interdental arch wiring involves the securing of the fragments of a broken jawbone with respect to one another using lengths of thin and malleable wire known as fracture wire. The wire is inserted laterally into and through the spaces between the patient's teeth (interdental spaces) and around the jawbone fragments. Typically, the ends of a relatively short length of fracture wire are inserted into the interdental spaces on opposite sides of a single tooth adjacent the gums and the wire is pulled into a U-shape around the tooth. In this way, the wire is anchored around a circumferential bar which allows fixation and stabilization of the fractured jaw portions. The essence of fracture repair is to produce immobility of the fractured portions by utilizing the wire loops to fix the fractured ends and the two jaws together via the rigid arch bars. In common practice all teeth present in both jaws are wired in standard fracture repair procedures.

The operation of inserting the fracture wire into an interdental space is awkward to perform. Not only must the surgeon manipulate the wire inside the patient's mouth but the characteristics of the wire itself make it difficult to insert. The wire cannot be rigid but must be at least fairly malleable in the sense that it can be readily deformed and has minimal tendency to return to its original shape. As a result, the wire will often tend to buckle as it is inserted axially between two teeth.

Insertion of fracture wire is not only inconvenient and frustrating from the viewpoint of the surgeon, but from the patient's viewpoint, speed in inserting the fracture wire is desirable because the technique of interdental arch wiring is normally performed under general anaesthesetic with the result that the patient is exposed to greater risk the longer the operation takes. It is therefore desirable to minimize the time required to instal the fracture wire.

As far as is known, the United States patent literature contains no prior proposal for facilitating this operation. The following U.S. patents were considered in the preparation of this application:

U.S. Pat. No. 3,762,418—William G. Wasson
U.S. Pat. No. 2,648,341—S. Moll
U.S. Pat. No. 454,327—M. M. Brown
U.S. Pat. No. 1,190,180—J. B. McAllister
U.S. Pat. No. 3,085,339—D. R. Wolfe
U.S. Pat. No. 2,481,177—B. F. Tofflemire An object of the present invention is to provide a device for use in interdental arch wiring designed to facilitate installation of the wire.

According to a broad aspect of the invention, there is provided a device for use in interdental arch wiring which includes a length of thin and malleable wire suitable for wiring a fractured jaw and having respectively opposite end portions. An elongate filament is secured to at least one of the wire end portions so as to effectively form a continuation of said portion. The filament is sufficiently thin and flexible to permit insertion thereof into an interdental space between two adjacent teeth by tensioning the filament across the interdental contact point between the teeth with the filament extending generally normal to a line joining the teeth, and drawing the tensioned filament downwardly through the interdental contact point, whereby the filament can then be used to lead the wire into the interdental space.

Preferably, the wire is formed into a U-shape and the filament is in the form of a loop, the ends of which are secured to the respective end portions of the wire. This allows respective portions of the filament adjacent the end portions of the wire to be introduced successively into adjacent interdental spaces on opposite sides of a tooth. By pulling on the filament loop, the end portions of the wire can then be led through the respective spaces until the bight of the wire embraces the tooth.

In order that the invention may be more clearly understood, reference will now be made to the accompanying drawings which illustrate a number of preferred embodiments of the invention by way of example, and in which.

Figure 1:
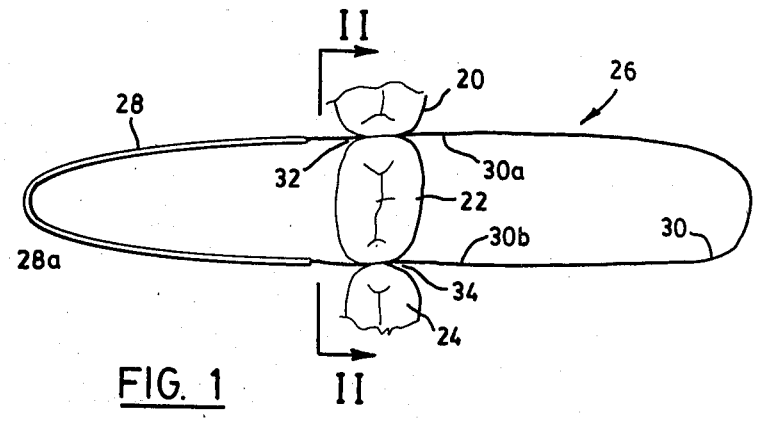
FIG. 1 is an occlusal (plan) view showing three adjacent teeth in a human jawbone with a device of the form provided by the invention in position preparatory to passing through the interdental contact points on opposite sides of the tooth shown at the centre.

Referring first to FIG. 1, three adjacent teeth in the lower jawbone of a human are indicated at 20, 22, and 24. Reference 26 indicates a device of the form provided by the invention in position preparatory to being engaged in the interdental spaces on opposite sides of the center tooth 22. Device 26 includes a U-shaped legnth of wire 28 and a filament loop 30, the ends of which are secured to respectively opposite end portions of wire 28. In the embodiment, wire 28 is a length of conventional fracture wire, having the characteristics of being relatively thin and yet possessing significant tensile strength. At the same time, the wire is malleable in the sense that it can be deformed while exhibiting relatively little tendency to return to its original shape. Filament 30 is a length of waxed or unwaxed dental floss.

Figure 2:
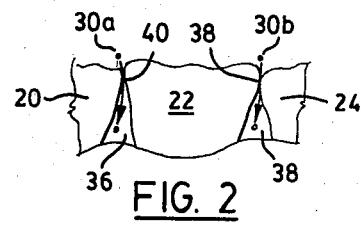
FIG. 2 is a view on line II—II of FIG. 1.

Device 26 is shown positioned with respective portions 30a and 30b of filament 30 adjacent end portions of wire 28 extending across the respective interdental contact points 32 and 34 between the center tooth 22 and the respective adjacent teeth 20 and 24. The filament portions extend generally normal to a line joining the teeth and are capable of being tensioned and drawn downwardly through the interdental contact points into the respective interdental spaces between tooth 22 and the teeth 20 and 24 as indicated at 36 and 38 respectively in FIG. 2. The arrows indicated at 40 and 42 indicate such downward movement of the filament portions 30a and 30b respectively.

In practice, the surgeon performing the interdental arch wiring operation will grasp a first one of the filament portions 30 and 30b on opposite sides of the relevant interdental contact point and exert downward pressure, possibly accompanied by longitudinal movement of the filament to bring the filament portion down into the interdental space in exactly the same manner as he would a length of dental floss. This operation is then repeated with the other filament portion adjacent to the opposite end of the filament loop. The two filament portions will then be positioned in the respective interdental spaces 36 and 38 as shown at the bottom in FIG. 2.

Figure 3:
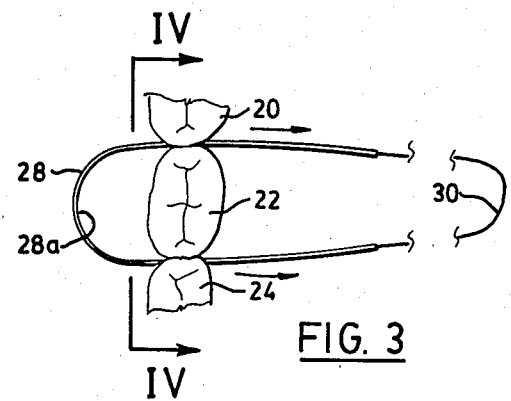
FIG. 3 is a view similar to FIG. 1 but showing the wire of the device partly installed in the interdental spaces.
Figure 4:
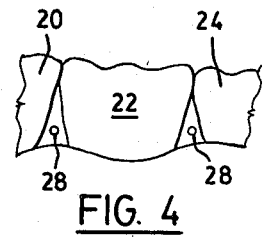
FIG. 4 is a view on line IV—IV of FIG. 3.

Next, by gently pulling on the filament loop to the right as shown in FIGS. 1 and 3, the respective end portions of the length of wire 28 are gently led into the interdental spaces, following the filament as it is withdrawn. FIGS. 3 and 4 show the device 26 in a position in which the end portions of wire 28 have moved partway through the respective interdental spaces 36 and 38. By continued movement of the filament and wire to the right as seen in FIG. 3, the bight 28a of wire 28 is brought into contact with and embraces tooth 22. The fracture wire is now in position and the dental floss can be cut off, leaving the wire ready to be secured to the rigid arch bar to stabilize the broken jaw fragment in the normal way.

Figure 5:
FIGS. 5 and 6 are detailed views showing alternative methods of securing the filament to the wire.
Figure 6:

The dental floss filament 30 may be secured to the wire 28 in any of a number of ways. FIGS. 5 and 6 show two of these ways. As seen in FIG. 5, an end portion 28b of wire 28 is shown in partial overlapping relationship with the corresponding end portion of filament portion 30a. The overlapping portions of the respective components are secured together by adhesive. In practice, Duro Superglue (trade mark) Adhesive was used. The outer end of the wire was sharpened to provide a taper for facilitating entry of the wire into the interdental space, although sharpening of the wire is not essential.

As seen in FIG. 6, the end portion 28b¹ of the wire is formed with an axial recess 44 into which the end portion of the filament is inserted and secured using the same adhesive. In an alternative embodiment, the wire could be crimped onto the filament. It will of course be understood that these attachment methods are given by way of example only and that many other methods could be used. For example, techniques conventionally used for securing a surgical suture to a needle could be used.

The particular materials from which the wire and filament respectively are made may vary provided that each has the characteristics required to fulfill the desired function. In practice, it has been found most convenient to use conventional fracture wire and dental floss as indicated above. A 4" length of fracture wire sharpened at each end and a 6" loop of unwaxed dental floss have been found to be suitable in practice. Obviously, the wire should be sufficiently long that it can be used to fulfil the required wiring function after it has been installed. Similarly, the dental floss should be of such a length that it can be readily grasped by the surgeon and manipulated into place.

It will of course be appreciated that, while the particular configuration of the device as shown in the drawings is believed to be preferred, there is no limitation to this particular configuration. In its simplest form, the device may comprise a length of wire having a filament attached to one end thereof only. The filament could then be inserted into one interdental space and used to pull the wire through that space. The wire could then be bent around and the same length of filament used to introduce the wire into the adjacent interdental space. Another alternative would be to use two separate lengths of filament attached to respectively opposite ends of the wire. The wire itself can of course be of any shape in the device as sold because it can be readily formed into the U-shape required for convenient installation.

I claim:

1. A device for use in interdental arch wiring, comprising:
    a length of thin and malleable wire suitable for wiring a fractured jaw, and having respectively opposite end portions, and
    an elongate filament having ends secured to respective ones of said wire end portions so as to effectively form continuations of said portions, said filament being sufficiently thin and flexible to permit insertion thereof into an interdental space between two adjacent teeth by tensioning the filament across the interdental contact point between the teeth with the filament extending generally normal to a line joining the teeth, and drawing the tensioned filament downwardly through the interdental contact point, whereby the filament can then be used to lead the wire into the interdental space.

2. A device as claimed in claim 1, wherein said length of wire is formed into an arch shaped loop.

3. A device as claimed in claim 1, wherein said filament is secured to said wire end portion in overlapping relationship by means of an adhesive.

4. A device as claimed in claim 3, wherein said end portion of the wire is sharpened to facilitate its entry into an interdental space.

5. A device as claimed in claim 1, wherein said wire end portion is formed with an axial opening in which said filament is secured.

6. A method of wiring a tooth in the performance of an interdental arch wiring technique, comprising:
    (1) providing a device comprising a generally U-shaped length of thin and malleable wire suitable for wiring a fractured jaw, and having respectively opposite end portions, and an elongate filament loop, ends of which are secured to said respectively opposite end portions of the wire so as to effectively form continuations of said portions, said filament being sufficiently thin and flexible to permit insertion thereof through each interdental contact point between said tooth and an immediately adjacent tooth and into the interdental space below said contact point;
    (2) inserting said length of wire into the interdental spaces on respectively opposite sides of said tooth by repeating the following steps in respect of each said space:
        (a) tensioning the filament across the relevant interdental contact point with the filament extending generally normal to a line joining the teeth;
        (b) drawing the tensioned filament downwardly through the interdental contact point; and,
        (c) pulling the filament laterally through said interdental space to lead the wire into said space.

7. A method as claimed in claim 6, wherein steps (a) and (b) are performed in respect of both said interdental spaces before step (c), and wherein portions of said wire are lead substantially simultaneously into both of said interdental spaces by pulling on said filament loop.

* * * * *